United States Patent
van der Veen et al.

(10) Patent No.: US 11,980,495 B2
(45) Date of Patent: May 14, 2024

(54) METHOD AND SYSTEM FOR PROVIDING ENHANCED COLOR FLOW DOPPLER AND PULSED WAVE DOPPLER ULTRASOUND IMAGES BY APPLYING CLINICALLY SPECIFIC FLOW PROFILES

(71) Applicant: GE Precision Healthcare LLC, Wauwatosa, WI (US)

(72) Inventors: Lucienne van der Veen, Ried im Innkreis (AT); Daniel Buckton, Salzburg (AT); Walter Duda, Jr., Regau (AT); Heinz Winkler-Ebner, Zipf (AT)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 0 days.

(21) Appl. No.: 16/860,277

(22) Filed: Apr. 28, 2020

(65) Prior Publication Data
US 2021/0330284 A1    Oct. 28, 2021

(51) Int. Cl.
*A61B 8/08*    (2006.01)
*A61B 8/00*    (2006.01)
*A61B 8/14*    (2006.01)

(52) U.S. Cl.
CPC ............ *A61B 8/0866* (2013.01); *A61B 8/14* (2013.01); *A61B 8/463* (2013.01); *A61B 8/488* (2013.01)

(58) Field of Classification Search
CPC ......... A61B 8/0866; A61B 8/14; A61B 8/463; A61B 8/488; A61B 8/06; A61B 8/5246; A61B 8/54; G16H 40/63; G16H 40/60
See application file for complete search history.

(56) References Cited

U.S. PATENT DOCUMENTS

| | | | | |
|---|---|---|---|---|
| 5,634,465 A | * | 6/1997 | Schmiesing | G01S 15/58 73/861.25 |
| 7,711,581 B2 | * | 5/2010 | Hood | G16H 40/63 705/3 |

(Continued)

FOREIGN PATENT DOCUMENTS

JP    2003284718 A  *  10/2003  ............... A61B 8/06

OTHER PUBLICATIONS

Edan Instrument, Inc., EdanUSA U50 Diagnostic Ultrasound System User Manual, Version 1.2, P/N: 01.54.455436-12, Release Date: Aug. 2012.*

(Continued)

*Primary Examiner* — Bo Joseph Peng
(74) *Attorney, Agent, or Firm* — McAndrews, Held & Malloy, Ltd.; Daniel Bissing; David Bates

(57) ABSTRACT

A system and method for enhancing color flow Doppler and pulsed wave Doppler ultrasound images acquired based on clinically-specific profiles of imaging parameters is provided. The method includes presenting selectable clinical objects at a display. Each of the selectable clinical objects may be associated with color flow Doppler and pulsed wave Doppler profiles. Each of the profiles may comprise imaging parameters for the associated clinical object. The method includes receiving a selection of one of the selectable clinical objects and retrieving the color flow Doppler and pulsed wave Doppler profiles associated with the selected clinical object. The method includes acquiring and presenting color flow Doppler ultrasound data based on the imaging parameters of the retrieved color flow Doppler profile. The method includes initiating a pulsed wave Doppler imaging mode, and acquiring and presenting pulsed wave Doppler ultrasound data based on the imaging parameters of the retrieved pulsed wave Doppler profile.

19 Claims, 5 Drawing Sheets

(56) References Cited

U.S. PATENT DOCUMENTS

| | | | | |
|---|---|---|---|---|
| 7,983,920 B2* | 7/2011 | Sinclair, II | ........ | H04M 1/72454 |
| | | | | 704/270 |
| 8,282,554 B2* | 10/2012 | Makin | ...................... | A61N 7/02 |
| | | | | 600/439 |
| 2002/0173721 A1* | 11/2002 | Grunwald | .............. | A61B 8/462 |
| | | | | 600/437 |
| 2003/0013959 A1* | 1/2003 | Grunwald | .............. | A61B 8/468 |
| | | | | 600/437 |

OTHER PUBLICATIONS

Toshiba, Operation Manual For Diagnostic Ultrasound System Aplio 500 Model TUS-A500, No. 2B77-004EN*M, 2014.*
General Electric Co., "LOGIQ E9 User Guide," Technical Publications, Direction 5496410-100, Rev. 1, Version R5, Jun. 17, 2014, 294 pages.
General Electric Co., "Venue 50 User Guide," Technical Publications, Direction 5492909-100, Rev. 4, Mar. 13, 2014, 115 pages.
General Electric Co., "Vivid E9 User Manual," Technical Publications, GB092107, Rev. 05, Aug. 18, 2015, 613 pages.
General Electric Co., "Voluson E10 Basic User Manual," Technical Publications, H48711DP, Rev. 6, Nov. 2018, 436 pages.
General Electric Co., "Voluson E8 Basic User Manual," Technical Publications, H48711DM, Rev. 6, Nov. 2018, 420 pages.

* cited by examiner

METHOD AND SYSTEM FOR PROVIDING ENHANCED COLOR FLOW DOPPLER AND PULSED WAVE DOPPLER ULTRASOUND IMAGES BY APPLYING CLINICALLY SPECIFIC FLOW PROFILES

FIELD

Certain embodiments relate to ultrasound imaging. More specifically, certain embodiments relate to a method and system providing enhanced color flow Doppler and pulsed wave Doppler ultrasound images. The ultrasound images may be acquired based on profiles of imaging parameters specific to a selected clinical object. In various embodiments, automated measurements of the ultrasound images are provided.

BACKGROUND

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

Existing ultrasound systems may include profiles having pre-defined imaging parameters applied during ultrasound image acquisition. For example, a user may select high, mid, or low velocity settings for application during a color flow Doppler ultrasound examination. However, existing profiles may not include settings for specific clinical objects (i.e., anatomical structures). For example, different clinical objects having similar flow velocities may have different settings for acquiring desirable ultrasound images. Moreover, in systems where a clinical object is selectable, the clinical object is associated with one profile limited to a specific imaging mode. However, desirable imaging parameters for a color flow Doppler ultrasound image of a particular clinical object are typically different from desirable imaging parameters for a pulsed wave Doppler ultrasound image of the same clinical object.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for enhancing color flow Doppler and pulsed wave Doppler ultrasound images acquired based on clinically specific profiles of imaging parameters, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
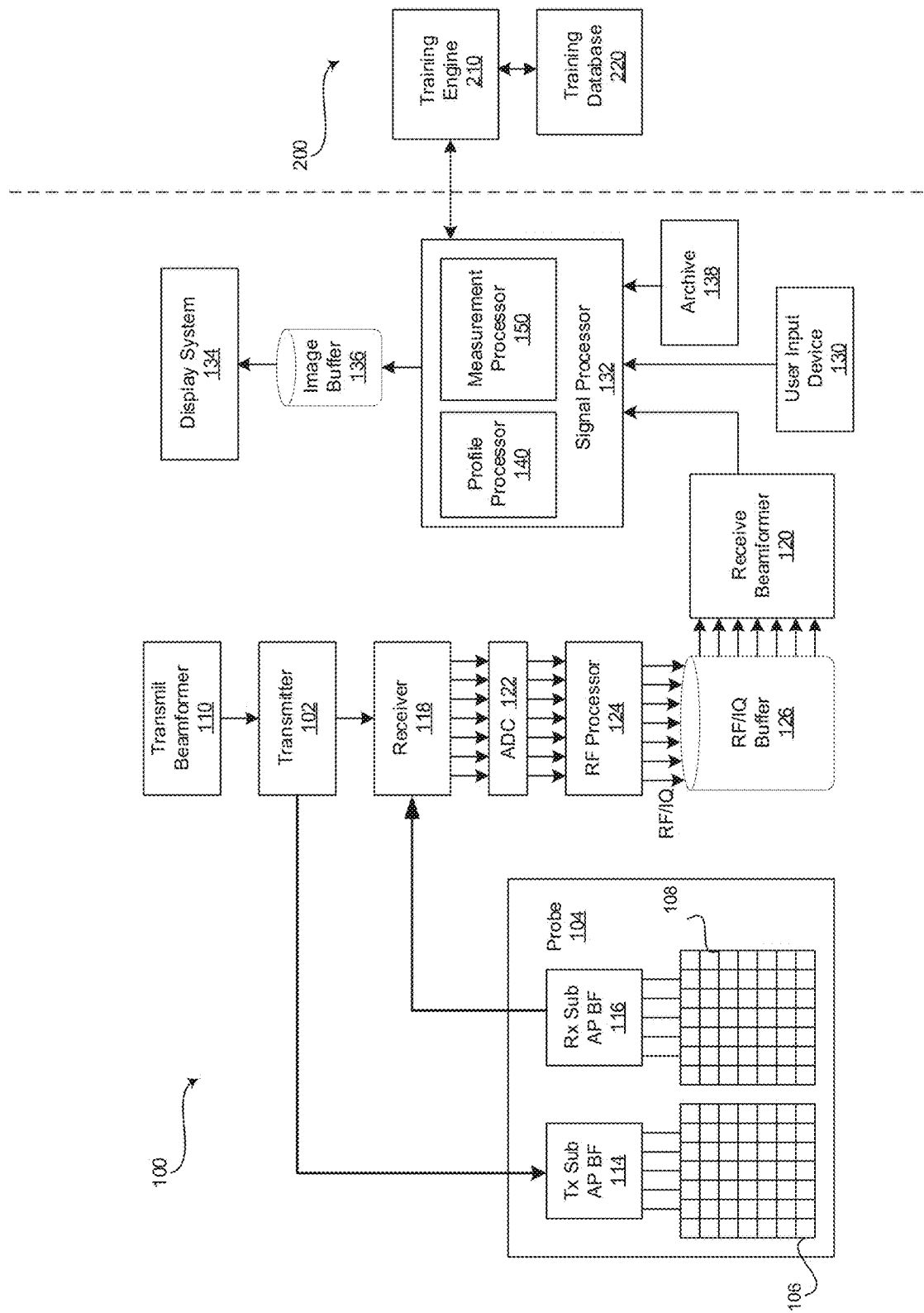
FIG. 1 is a block diagram of an exemplary ultrasound system and training system that is operable to enhance color flow Doppler and pulsed wave Doppler ultrasound images acquired based on clinically specific profiles of imaging parameters, in accordance with various embodiments.

Certain embodiments may be found in a method and system for enhancing color flow Doppler and pulsed wave Doppler ultrasound images acquired based on clinically specific profiles of imaging parameters. Various embodiments have the technical effect of providing profiles of imaging parameters optimized for color flow Doppler and pulsed wave Doppler ultrasound acquisitions of specific clinical objects. Aspects of the present disclosure have the technical effect of providing automated measurements of clinical objects depicted in color flow Doppler and/or pulsed wave Doppler ultrasound images.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, Contrast Enhanced Ultrasound (CEUS), and/or sub-modes of B-mode and/or CF such as Harmonic Imaging, Shear Wave Elasticity Imaging (SWEI), Strain Elastography, TVI, PDI, B-flow, MVI, UGAP, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphic Processing Unit (GPU), DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 and training system 200 that is operable to enhance color flow Doppler and pulsed wave Doppler ultrasound images acquired based on clinically specific profiles of imaging parameters, in accordance with various embodiments. Referring to FIG. 1, there is shown an ultrasound system 100 and a training system 200. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and, an archive 138.

The transmitter 102 may comprise suitable logic, circuitry, interfaces and/or code that may be operable to drive an ultrasound probe 104. The ultrasound probe 104 may comprise a two-dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as a fetus, a heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or a plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, select clinical objects associated with profiles having imaging parameters, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134 or the ultrasound probe 104, for example. As an example, user input device 130 may include a touchscreen display. In a representative embodiment, user input device 130 may be configured to select one of a plurality of clinical objects, each of the clinical objects associated with profiles of pre-defined imaging parameters for application during acquisition of color flow Doppler and pulsed wave Doppler ultrasound examinations.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, graphic processing units, microprocessors, microcontrollers, and/or the like. The signal processor 132 may be an integrated component, or may be distributed across various locations, for example. In an exemplary embodiment, the signal processor 132 may comprise a profile processor 140 and a measurement processor 150 and may be capable of receiving input information from a user input device 130 and/or archive 138, generating an output displayable by a display system 134, and manipulating the output in response to input information from a user input device 130, among other things. The signal processor 132, profile processor 140, and measurement processor 150 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a profile processor 140 that comprises suitable logic, circuitry, interfaces and/or code that may be operable to present selectable clinical objects at the display system 134. For example, the selectable clinical objects may be presented at the display system 134 when the ultrasound system is operating in color flow Doppler and/or B-modes. The selectable clinical objects may be presented at the display system 134 as icons, labeled text boxes, in a list format, in a drop-down box, or any suitable selectable format. The selection of a selectable clinical object in B-mode by the profile processor 140 may cause the profile processor 140 to initiate the color flow Doppler mode. The selectable clinical objects may be anatomical structures of interest in an obstetrics ultrasound examination, such as a uterine artery, a middle cerebral artery, an umbilical artery, a ductus venosis, an aorta, or the like. Each of the selectable clinical objects is associated with a color flow Doppler profile and pulsed wave Doppler profile. Each of the color flow Doppler and pulsed wave Doppler profiles comprises pre-defined imaging parameters. For example, the color flow Doppler profiles may include a pulse repetition frequency (PRF), frequency, wall motion filter setting, gain, and the like. The pulsed wave Doppler profiles may include a PRF, frequency, wall motion filter setting, baseline, gain, gate size, and the like. In various embodiments, the profiles may include clinically appropriate measurements, such as a peak systolic velocity (PS), end-diastolic velocity (ED), min-diastolic velocity (MD), ratio (S/D) of peak systolic velocity to end-diastolic velocity (PS/ED), pulsatility index (PI), resistivity index (RI), time averaged maximum velocity ($TA_{MAX}$), heart rate, and/or any suitable measurement. In various embodiments, additional profiles may be provided and selected based on the selected clinical object and patient information, such as a gestational age of a fetus, or any suitable patient information. The color flow Doppler and pulsed wave Doppler profiles may be stored in archive 138 and/or any suitable data storage medium for retrieval by the profile processor 140 in response to a user input selecting one of the selectable clinical objects.

The profile processor 140 comprises suitable logic, circuitry, interfaces and/or code that may be operable to retrieve profiles associated with the selectable clinical objects in response to a selection. For example, the profile processor 140 may receive a selection via user input device 130 of one of the selectable clinical objects presented at the display system 134, such as the uterine artery clinical object. The profile processor 140 retrieves the color flow Doppler and pulsed wave Doppler profiles associated with the uterine artery clinical object from the archive 138 and/or any suitable data storage medium. In various embodiments, the retrieved profile may be based in part on patient information, such as a gestational age of a fetus, or any suitable patient information.

The profile processor 140 comprises suitable logic, circuitry, interfaces and/or code that may be operable to apply the retrieved profiles to acquire and present color flow Doppler ultrasound images and pulsed wave Doppler ultrasound images. For example, a user may select one of the selectable clinical objects, such as an umbilical artery, and the profile processor 140 may retrieve the color flow Doppler and pulsed wave Doppler profiles as described above. The user may manipulate the ultrasound probe 104 to acquire ultrasound data of the umbilical artery and the profile processor 140 may apply the pre-defined imaging parameters of the color flow Doppler profile associated with the umbilical artery clinical object to acquire, process, and present the color flow Doppler ultrasound data at the display system 134. The user, via the user input device 130, may initiate pulsed wave Doppler mode by, for example, placing a gate in the color flow Doppler ultrasound image, selecting a pulsed wave Doppler start button, and/or the like and the profile processor 140 may apply the pre-defined imaging parameters of the pulsed wave Doppler profile associated with the umbilical artery clinical object to acquire, process, and present the pulsed wave Doppler ultrasound data at the display system 134.

The signal processor 132 may include a measurement processor 150 that comprises suitable logic, circuitry, interfaces and/or code that may be operable to automatically provide measurements of clinical objects depicted in color flow Doppler and/or pulsed wave Doppler ultrasound images. The measurements performed by the measurement processor 150 may be specified in, for example, the color flow Doppler and/or pulsed wave Doppler profiles, a selected protocol, and/or any suitable technique for defining desired measurements of a selected clinical object. The measurements may be performed by the measurement processor 150 executing image recognition algorithms, artificial intelligence, and/or any suitable image recognition technique. For example, the measurement processor 150 may deploy deep neural network(s) (e.g., artificial intelligence model(s)) that may be made up of, for example, an input layer, an output layer, and one or more hidden layers in between the input and output layers. Each of the layers may be made up of a plurality of processing nodes that may be referred to as neurons. For example, the measurement processor 150 may inference an artificial intelligence model comprising an input layer having a neuron for each pixel or a group of pixels from a scan plane of a clinical object. The output layer may have neurons corresponding to a measurement of the clinical object. As an example, the output layer may provide a peak systolic velocity (PS) measurement, end-diastolic velocity (ED) measurement, min-diastolic velocity (MD) measurement, ratio (S/D) of peak systolic velocity to end-diastolic velocity (PS/ED) measurement, pulsatility index (PI) measurement, resistivity index (RI) measurement, time averaged maximum velocity ($TA_{MAX}$) measurement, heart rate measurement, and/or any suitable measurement. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the measurement processor 150 inferencing the deep neural network (e.g., convolutional neural network) may provide measurements of clinical objects in color flow Doppler and/or pulsed wave Doppler ultrasound image data with a high degree of probability.

Figure 2:
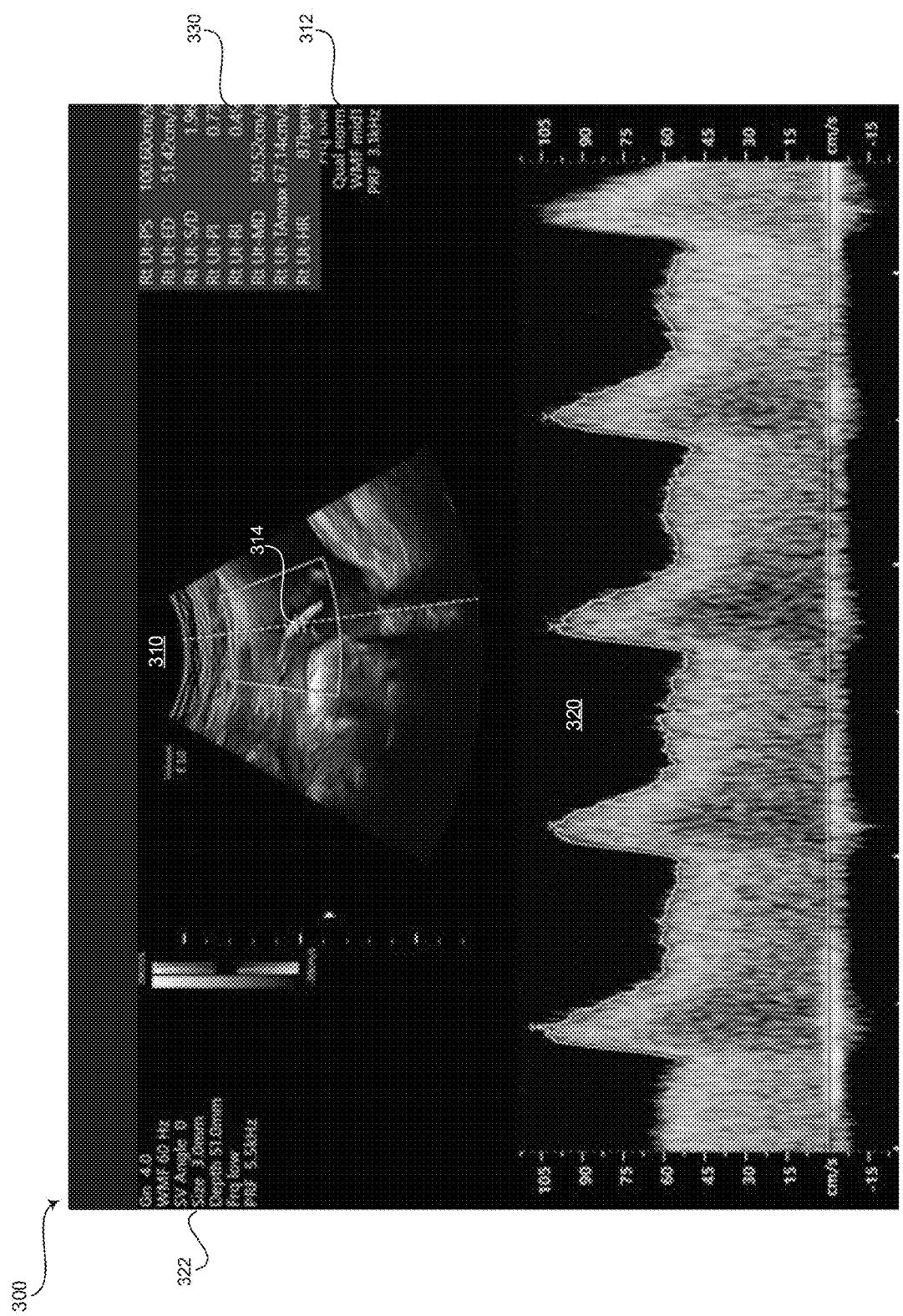
FIG. 2 is an exemplary display of a color flow Doppler ultrasound image of a uterine artery, a pulsed wave Doppler ultrasound image of the uterine artery, and uterine artery measurements, in accordance with various embodiments.
Figure 3:
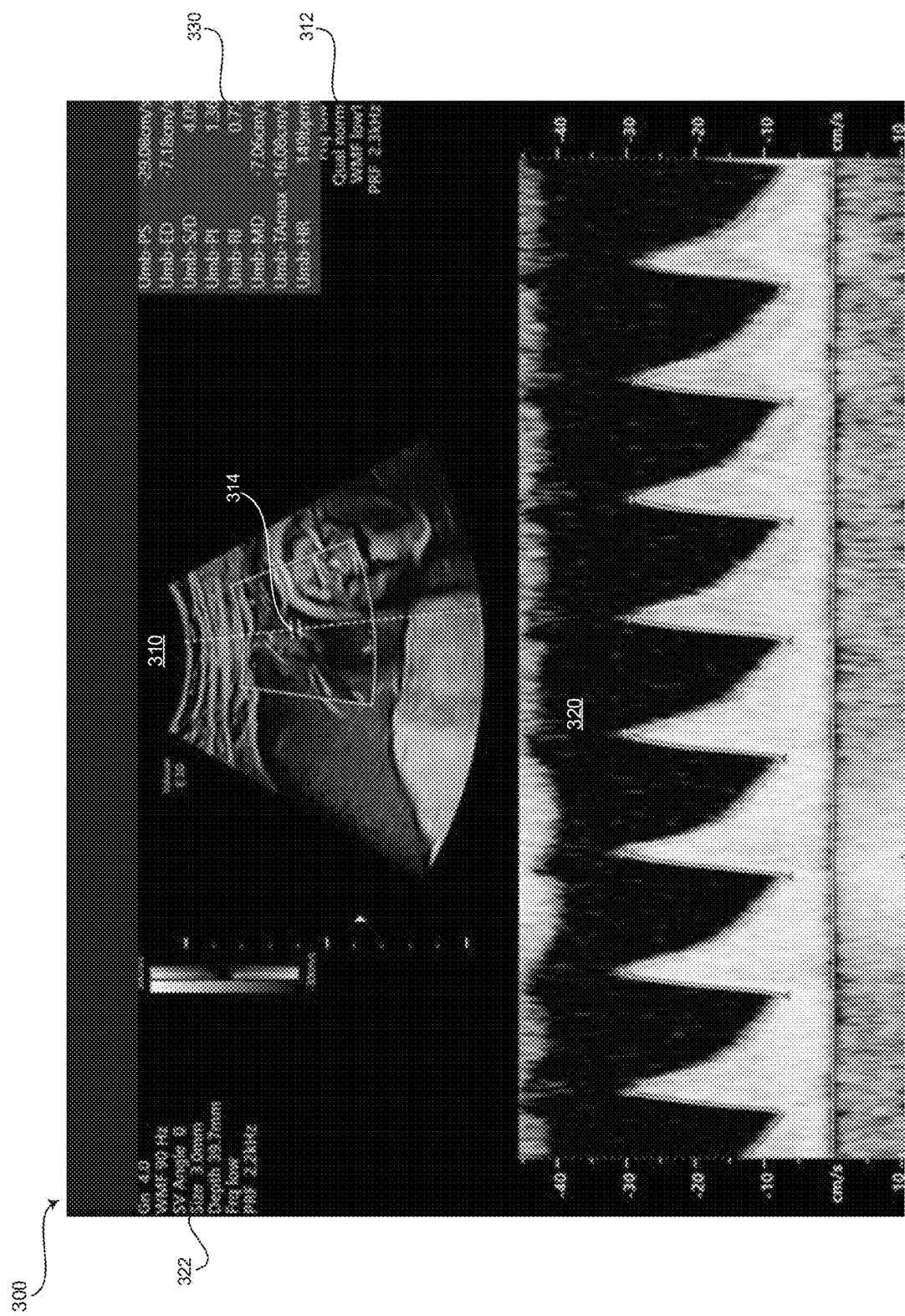
FIG. 3 is an exemplary display of a color flow Doppler ultrasound image of an umbilical artery, a pulsed wave Doppler ultrasound image of the umbilical artery, and umbilical artery measurements, in accordance with various embodiments.
Figure 4:
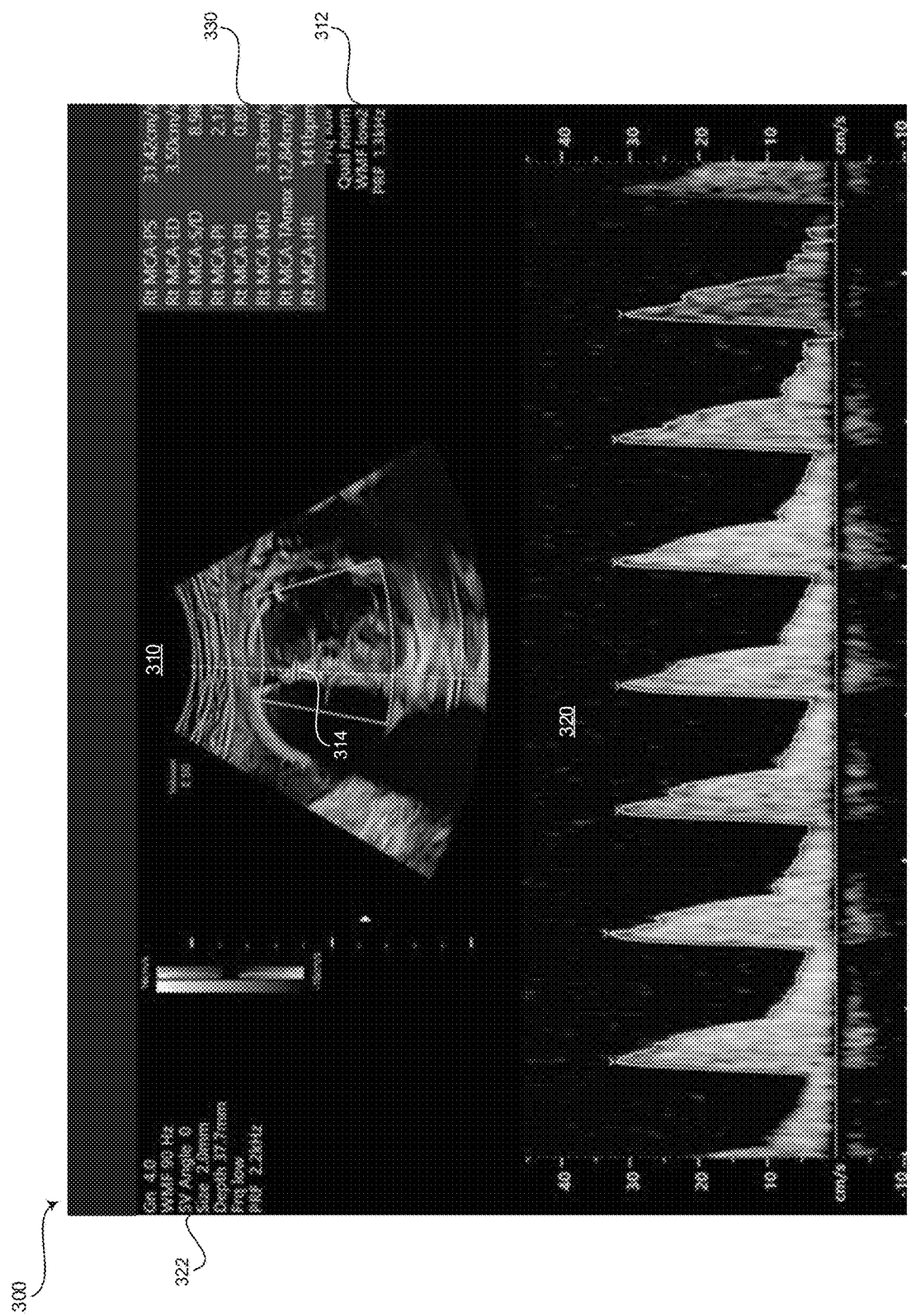
FIG. 4 is an exemplary display of a color flow Doppler ultrasound image of a middle cerebral artery, a pulsed wave Doppler ultrasound image of the middle cerebral artery, and middle cerebral artery measurements, in accordance with various embodiments.

FIG. 2 is an exemplary display 300 of a color flow Doppler ultrasound image 310 of a uterine artery, a pulsed wave Doppler ultrasound image 320 of the uterine artery, and uterine artery measurements 330, in accordance with various embodiments. FIG. 3 is an exemplary display 300 of a color flow Doppler ultrasound image 310 of an umbilical artery, a pulsed wave Doppler ultrasound image 320 of the umbilical artery, and umbilical artery measurements 330, in accordance with various embodiments. FIG. 4 is an exemplary display 300 of a color flow Doppler ultrasound image 310 of a middle cerebral artery, a pulsed wave Doppler ultrasound image 320 of the middle cerebral artery, and middle cerebral artery measurements 330, in accordance with various embodiments.

Referring to FIGS. 2-4, the display 300 may include a color flow Doppler ultrasound image 310, a pulsed wave Doppler ultrasound image 320, and measurements of the clinical object 330. The color flow Doppler ultrasound image 310 may be acquired according to imaging parameters 312 of the color flow Doppler profile corresponding with the particular clinical object (i.e., uterine artery in FIG. 2, umbilical artery in FIG. 3, and middle cerebral artery in FIG. 4). The pulsed wave Doppler ultrasound image 320 may correspond to the gate 314 positioned in the color flow Doppler ultrasound image 310. The pulsed wave Doppler ultrasound image 320 may be acquired according to imaging parameters 322 of the pulsed wave Doppler profile corresponding with the particular clinical object (i.e., uterine artery in FIG. 2, umbilical artery in FIG. 3, and middle cerebral artery in FIG. 4). The measurements 330 may be automatically performed by a measurement processor 150 of a signal processor 132 of the ultrasound system 100 and may include, for example, a peak systolic velocity (PS) measurement, end-diastolic velocity (ED) measurement, min-diastolic velocity (MD) measurement, ratio (S/D) of peak systolic velocity to end-diastolic velocity (PS/ED) measurement, pulsatility index (PI) measurement, resistivity index (RI) measurement, time averaged maximum velocity ($TA_{MAX}$) measurement, heart rate measurement, and/or any suitable measurement. The color flow Doppler ultrasound image 310, the pulsed wave Doppler ultrasound image 320, and measurements of the clinical object 330 may be presented at a display 300 of the display system 134 and/or stored at archive 134 or any suitable data storage medium.

Referring again to FIG. 1, the display system 134 may be any device capable of communicating visual information to a user. For example, a display system 134 may include a liquid crystal display, a light emitting diode display, and/or any suitable display or displays. The display system 134 can be operable to present selectable clinical objects, color flow Doppler ultrasound images, pulsed wave Doppler ultrasound images, measurements, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores color flow Doppler profiles, pulsed wave Doppler profiles, instructions for presenting clinical objects, instructions for retrieving profiles in response to clinical object selections, instructions for applying profiles to acquire, process, and present ultrasound images, color flow Doppler ultrasound images, pulsed wave Doppler ultrasound images, and/or artificial intelligence models deployable to perform measurements, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Still referring to FIG. 1, the training system 200 may comprise a training engine 210 and a training database 220. The training engine 160 may comprise suitable logic, circuitry, interfaces and/or code that may be operable to train the neurons of the deep neural network(s) (e.g., artificial intelligence model(s)) inferenced (i.e., deployed) by the measurement processor 150. For example, the artificial intelligence model inferenced by the measurement processor 150 may be trained to automatically perform measurements of selected clinical objects. As an example, the training engine 210 may train the deep neural networks deployed by the measurement processor 150 using database(s) 220 of classified ultrasound images of various clinical objects and measurements of the various clinical objects. The ultrasound images may include clinical objects of interest in an obstetrics ultrasound examination, such as a uterine artery, a middle cerebral artery, an umbilical artery, a ductus venosis, an aorta, or the like. The measurements may include a peak systolic velocity (PS) measurement, end-diastolic velocity (ED) measurement, min-diastolic velocity (MD) measurement, ratio (S/D) of peak systolic velocity to end-diastolic velocity (PS/ED) measurement, pulsatility index (PI) measurement, resistivity index (RI) measurement, time averaged maximum velocity ($TA_{MAX}$) measurement, heart rate measurement, and/or any suitable measurement.

In various embodiments, the databases 220 of training images may be a Picture Archiving and Communication System (PACS), or any suitable data storage medium. In certain embodiments, the training engine 210 and/or training image databases 220 may be remote system(s) communicatively coupled via a wired or wireless connection to the ultrasound system 100 as shown in FIG. 1. Additionally and/or alternatively, components or all of the training system 200 may be integrated with the ultrasound system 100 in various forms.

Figure 5:
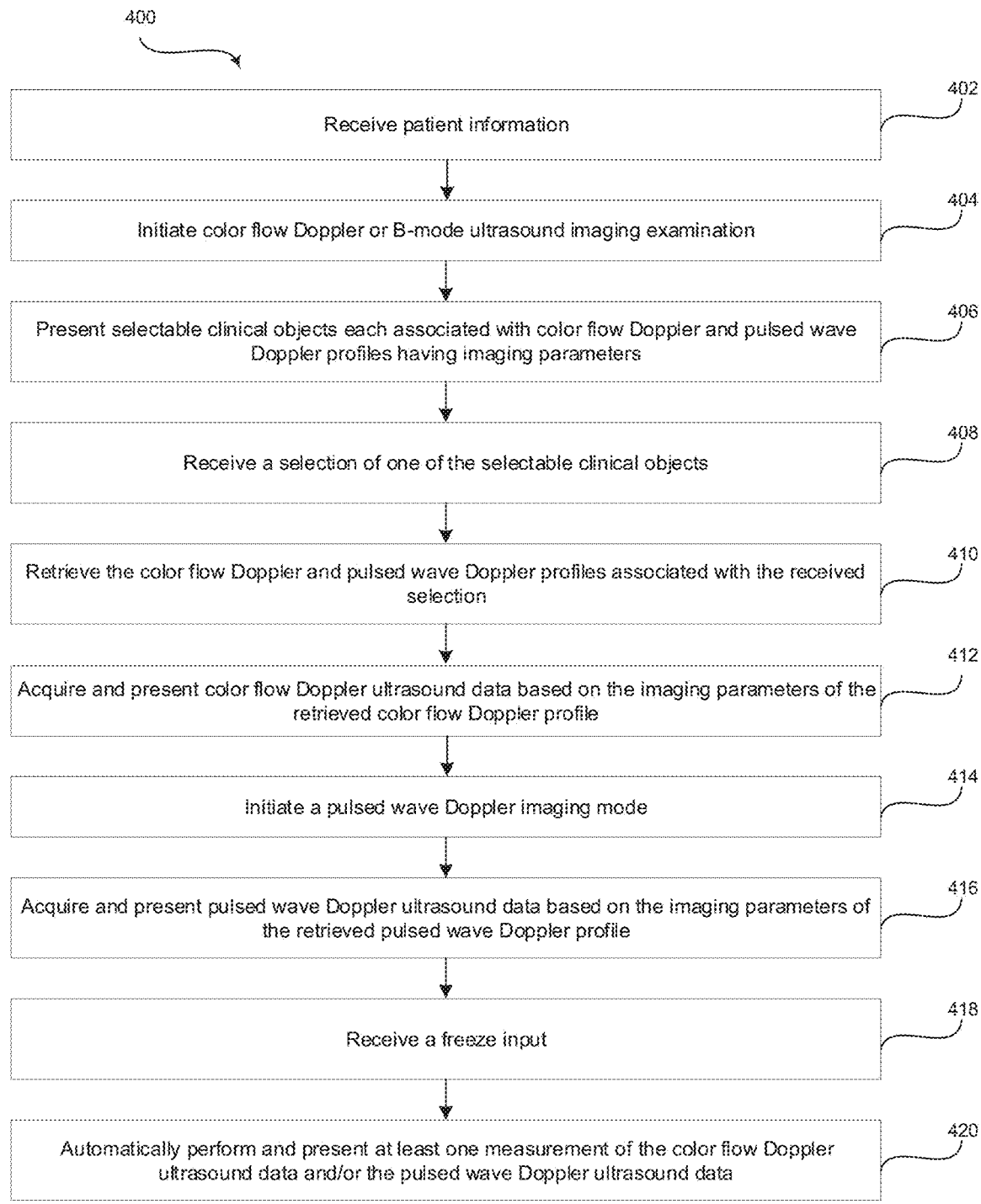
FIG. 5 is a flow chart illustrating exemplary steps that may be utilized for enhancing color flow Doppler and pulsed wave Doppler ultrasound images acquired based on clinically specific profiles of imaging parameters, in accordance with various embodiments.

FIG. 5 is a flow chart 400 illustrating exemplary steps 402-420 that may be utilized for enhancing color flow Doppler 310 and pulsed wave Doppler 320 ultrasound images acquired based on clinically specific profiles of imaging parameters, in accordance with various embodiments. Referring to FIG. 5, there is shown a flow chart 400 comprising exemplary steps 402 through 420. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 402, a signal processor 132 of an ultrasound system 100 receives patient information. For example, the patient information may be related to an ultrasound procedure to be performed. The patient information may include a patient name, age, sex, procedure type, the gestational age of a fetus (for obstetrics), and/or any suitable patient information.

At step 404, the signal processor 132 of the ultrasound system initiates a color flow Doppler or B-mode ultrasound imaging examination. For example, the signal processor 132 may receive a user input via user input device 130 selecting an ultrasound image mode. The signal processor 132 initiates the selected imaging mode in response to the received user input.

At step 406, the signal processor 132 of the ultrasound system 100 may present selectable clinical objects each associated with color flow Doppler and pulsed wave Doppler profiles having imaging parameters. For example, a profile processor 140 of the signal processor 132 may present the selectable clinical objects at a display system 134 of the ultrasound system 100. The selectable clinical objects may be presented at the display system 134 as icons, labeled text boxes, in a list format, in a drop-down box, or any suitable selectable format. The selectable clinical objects may be anatomical structures of interest in an obstetrics ultrasound examination, such as a uterine artery, a middle cerebral artery, an umbilical artery, a ductus venosis, an aorta, or the like. Each of the selectable clinical objects is associated with a color flow Doppler profile and pulsed wave Doppler profile. Each of the color flow Doppler and pulsed wave Doppler profiles comprises pre-defined imaging parameters. In various embodiments, the profiles may include clinically appropriate measurements.

At step 408, the signal processor 132 of the ultrasound system 100 may receive a selection of one of the selectable clinical objects. For example, the profile processor 140 of the signal processor 132 may receive a selection via the user input device 130 of one of the displayed clinical objects, such as a uterine artery, a middle cerebral artery, an umbilical artery, a ductus venosis, an aorta, or the like. The selection of a selectable clinical object in B-mode by the profile processor 140 may cause the profile processor 140 to initiate the color flow Doppler mode.

At step 410, the signal processor 132 of the ultrasound system 100 may retrieve the color flow Doppler and pulsed wave Doppler profiles associated with the received selection. For example, the profile processor 140 of the signal processor 132 may retrieve the color flow Doppler and pulsed wave Doppler profiles associated with the clinical object selected at step 408 from archive 138 and/or any suitable data storage medium. In various embodiments, the profile processor 140 may retrieve the color flow Doppler and pulsed wave Doppler profiles based on the clinical object selected at step 408 and the patient information provided at step 402, such as a gestational age of a fetus, or any suitable patient information.

At step 412, the ultrasound system 100 acquires and presents color flow Doppler ultrasound data 310 based on the imaging parameters 312 of the retrieved color flow Doppler profile. For example, the ultrasound system 100 may acquire color flow Doppler ultrasound data 310 with an ultrasound probe 104 positioned at a scan position over the clinical object of interest based on the imaging parameters 312 of the color flow Doppler profile applied by the profile processor 140 of the signal processor 132. The acquired color flow Doppler ultrasound data 310 may be processed and presented by the profile processor 140 at a display 300 of the display system 134.

At step 414, the signal processor 132 of the ultrasound system 100 initiates a pulsed wave Doppler imaging mode. For example, the signal processor 132 and/or the profile processor 140 may initiate pulsed wave Doppler mode in response to receiving, via the user input device 130, a gate 314 placement in the color flow Doppler ultrasound image 310, a selection of a pulsed wave Doppler start button, and/or the like.

At step 416, the ultrasound system 100 acquires and presents pulsed wave Doppler ultrasound data 320 based on the imaging parameters 322 of the retrieved pulsed wave Doppler profile. For example, the ultrasound system 100 may acquire pulsed wave Doppler ultrasound data 320 with an ultrasound probe 104 positioned at a scan position over the clinical object of interest based on the imaging parameters 322 of the pulsed wave Doppler profile applied by the profile processor 140 of the signal processor 132. The acquired pulsed wave Doppler ultrasound data 320 may be processed and presented by the profile processor 140 at a display 300 of the display system 134.

At step 418, the signal processor 132 of the ultrasound system 100 receives a freeze input. For example, the signal processor 132 may freeze the display of the pulsed wave Doppler ultrasound data 320 and/or the color flow Doppler ultrasound data 310 in response to receiving, via the user input device 130, a freeze input from a user.

At step 420, the signal processor 132 of the ultrasound system 100 automatically performs and presents at least one measurement 330 of the color flow Doppler ultrasound data 310 and/or the pulsed wave Doppler ultrasound data 320. For example, the measurement processor 150 of the signal processor 132 may be operable to automatically provide measurements 330 of clinical objects depicted in color flow Doppler and/or pulsed wave Doppler ultrasound images. The measurements 330 performed by the measurement processor 150 may be specified in, for example, the color flow Doppler and/or pulsed wave Doppler profiles, a selected protocol, and/or any suitable technique for defining desired measurements of a selected clinical object. The measurements 330 may be performed by the measurement processor 150 executing image recognition algorithms, artificial intelligence, and/or any suitable image recognition technique. The measurement processor 150 may present the measurements 330 at a display 300 of the display system 134 and/or store the measurements in archive 138 and/or any suitable data storage medium. The measurements 330 may include a peak systolic velocity (PS) measurement, end-diastolic velocity (ED) measurement, min-diastolic velocity (MD) measurement, ratio (S/D) of peak systolic velocity to end-diastolic velocity (PS/ED) measurement, pulsatility index (PI) measurement, resistivity index (RI) measurement, time averaged maximum velocity ($TA_{MAX}$) measurement, heart rate measurement, and/or any suitable measurement.

Aspects of the present disclosure provide a method 400 and system 100 for enhancing color flow Doppler 310 and pulsed wave Doppler 320 ultrasound images acquired based on clinically specific profiles of imaging parameters. In accordance with various embodiments, the method 400 may comprise presenting 406, by at least one processor 1320, 140 of an ultrasound system 100, a plurality of selectable clinical objects at a display system 134. Each of the plurality of selectable clinical objects may be associated with a color flow Doppler profile and a pulsed wave Doppler profile. Each of the color flow Doppler profile and the pulsed wave Doppler profile may comprise imaging parameters 312, 322 for the associated one of the plurality of selectable clinical objects. The method 400 may comprise receiving 408, by the at least one processor 132, 140, a selection of one of the plurality of selectable clinical objects. The method 400 may comprise retrieving 410g, by the at least one processor 132, 140, the color flow Doppler profile and the pulsed wave Doppler profile associated with the selected one of the plurality of selectable clinical objects. The method 400 may comprise acquiring, by the ultrasound system 100, and presenting 412, at the display system 134, color flow Doppler ultrasound data 310 based on the imaging parameters 312 of the retrieved color flow Doppler profile. The method 400 may comprise initiating 414, by the at least one processor 132, 140, a pulsed wave Doppler imaging mode. The method 400 may comprise acquiring, by the ultrasound system 100, and presenting 416, at the display system 134, pulsed wave Doppler ultrasound data 320 based on the imaging parameters 322 of the retrieved pulsed wave Doppler profile.

In an exemplary embodiment, the method 400 may comprise receiving 402, by the at least one processor 132, patient information comprising a gestational age of a fetus. The color flow Doppler profile and the pulsed wave Doppler profile may be retrieved based in part on the gestational age of the fetus. In various embodiments, the pulsed wave Doppler imaging mode may be initiated in response to receiving a placement of a gate 314 in the color flow Doppler ultrasound data 310. In certain embodiments, the method 400 may comprise initiating 404, by the at least one processor 132, a B-mode ultrasound imaging mode prior to presenting 406 the plurality of selectable clinical objects at the display system 134. The method 400 may comprise switching 408-412, by the at least one processor 132, 140, to a color flow Doppler imaging mode after receiving 408 the selection of the one of the plurality of selectable clinical objects. In a representative embodiment, the plurality of selectable clinical objects may comprise a plurality of a uterine artery, a middle cerebral artery, an umbilical artery, a ductus venosis, and an aorta. In a representative embodiment, the imaging parameters 312, 322 of the color flow Doppler profile and the pulsed wave Doppler profile may each comprise a plurality of a pulse repetition frequency (PRF), a frequency, a wall motion filter setting, a baseline, a gain, and a gate size. In an exemplary embodiment, the method 400 may comprise receiving 418, by the at least one processor 132, 140, 150, a freeze input. The method 400 may comprise automatically performing, by the at least one processor 132, 150, and presenting 420, at the display system 134, at least one measurement 330 of the color flow Doppler ultrasound data and/or the pulsed wave Doppler ultrasound data. In certain embodiments, the at least one measurement 330 may comprise a peak systolic velocity (PS) measurement, an end-diastolic velocity (ED) measurement, a min-diastolic velocity (MD) measurement, a ratio (S/D) of peak systolic velocity to end-diastolic velocity (PS/ED) measurement, a pulsatility index (PI) measurement, a resistivity index (RI) measurement, and/or a time averaged maximum velocity ($TA_{MAX}$) measurement.

Various embodiments provide a system 100 for enhancing color flow Doppler and pulsed wave Doppler ultrasound images acquired based on clinically specific profiles of imaging parameters. The ultrasound system 100 may comprise a display system 134 and at least one processor 132, 140, 150. The display system 134 may be configured to present a plurality of selectable clinical objects. Each of the plurality of selectable clinical objects may be associated with a color flow Doppler profile and a pulsed wave Doppler profile. Each of the color flow Doppler profile and the pulsed wave Doppler profile may comprise imaging parameters 312, 322 for the associated one of the plurality of selectable clinical objects. The at least one processor 132, 140 may be configured to receive a selection of one of the plurality of selectable clinical objects. The at least one processor 132, 140 may be configured to retrieve the color flow Doppler profile and the pulsed wave Doppler profile associated with the selected one of the plurality of selectable clinical objects. The at least one processor 132, 140 may be configured to apply the imaging parameters 312 of the retrieved color flow Doppler profile to acquire and present color flow Doppler ultrasound data 310 at the display system 134. The at least one processor 132, 140 may be configured to initiate a pulsed wave Doppler imaging mode. The at least one processor 132, 140 may be configured to apply the imaging parameters 322 of the retrieved pulsed wave Doppler profile to acquire and present pulsed wave Doppler ultrasound data 320 at the display system 134.

In a representative embodiment, the at least one processor 132 may be configured to receive patient information comprising a gestational age of a fetus. The color flow Doppler profile and the pulsed wave Doppler profile may be retrieved based in part on the gestational age of the fetus. In an exemplary embodiment, the at least one processor 132, 140 may be configured to initiate the pulsed wave Doppler imaging mode in response to receiving a placement of a gate 314 in the color flow Doppler ultrasound data 310. In various embodiments, the plurality of selectable clinical objects may comprise a plurality of a uterine artery, a middle cerebral artery, an umbilical artery, a ductus venosis, and an aorta. In certain embodiments, the imaging parameters 312, 314 of the color flow Doppler profile and the pulsed wave Doppler profile may each comprise a plurality of a pulse repetition frequency (PRF), a frequency, a wall motion filter setting, a baseline, a gain, and a gate size. In a representative embodiment, the at least one processor 132, 140, 150 may be configured to receive a freeze input. The at least one processor 132, 150 automatically perform and present at least one measurement 330 of the color flow Doppler ultrasound data 310 and/or the pulsed wave Doppler ultrasound data 320 at the display system 134. In various embodiments, the at least one measurement 330 may comprise a peak systolic velocity (PS) measurement, an end-diastolic velocity (ED) measurement, a min-diastolic velocity (MD) measurement, a ratio (S/D) of peak systolic velocity to end-diastolic velocity (PS/ED) measurement, a pulsatility index (PI) measurement, a resistivity index (RI) measurement, and/or a time averaged maximum velocity ($TA_{MAX}$) measurement.

Certain embodiments provide a non-transitory computer readable medium having stored thereon, a computer program having at least one code section. The at least one code section is executable by a machine for causing the machine to perform steps 400. The steps 400 may comprise presenting 406 a plurality of selectable clinical objects at a display system 134. Each of the plurality of selectable clinical objects may be associated with a color flow Doppler profile and a pulsed wave Doppler profile. Each of the color flow Doppler profile and the pulsed wave Doppler profile may comprise imaging parameters 312, 322 for the associated one of the plurality of selectable clinical objects. The steps 400 may comprise retrieving 410 the color flow Doppler profile and the pulsed wave Doppler profile associated with a selected one of the plurality of selectable clinical objects. The steps 400 may comprise acquiring and presenting 412, at the display system 134, color flow Doppler ultrasound data 310 based on the imaging parameters 312 of the retrieved color flow Doppler profile. The steps 400 may comprise initiating 414 a pulsed wave Doppler imaging mode. The steps 400 may comprise acquiring and presenting 416, at the display system 134, pulsed wave Doppler ultrasound data 320 based on the imaging parameters 322 of the retrieved pulsed wave Doppler profile.

In various embodiments, the steps 400 may comprise receiving 402 patient information comprising a gestational age of a fetus. The color flow Doppler profile and the pulsed wave Doppler profile may be retrieved 410 based in part on the gestational age of the fetus. In certain embodiments, the pulsed wave Doppler imaging mode is initiated 414 in response to receiving a placement of a gate 314 in the color flow Doppler ultrasound data 310. In an exemplary embodiment, the steps 400 may comprise initiating 404 a B-mode ultrasound imaging mode prior to presenting 406 the plurality of selectable clinical objects at the display system 134. The steps 400 may comprise switching 408-412 to a color flow Doppler imaging mode after receiving 408 a selection of the one of the plurality of selectable clinical objects. In a representative embodiment, the steps 400 may comprise receiving 418 a freeze input. The steps 400 may comprise automatically performing and presenting 420, at the display system 134, at least one measurement 330 of the color flow Doppler ultrasound data 310 and/or the pulsed wave Doppler ultrasound data 320.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for enhancing color flow Doppler and pulsed wave Doppler ultrasound images acquired based on clinically specific profiles of imaging parameters.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
presenting, by at least one processor of an ultrasound system, a plurality of selectable clinical objects at a display system, each of the plurality of selectable clinical objects is a different, specific anatomical structure, each of the plurality of selectable clinical objects associated with a color flow Doppler profile and a pulsed wave Doppler profile, each of the color flow Doppler profile and the pulsed wave Doppler profile comprising imaging parameters for the associated one of the plurality of selectable clinical objects, wherein one or both of the color flow Doppler profile or the pulsed wave Doppler profile specify a measurement of the specific anatomical structure to be automatically performed after receiving a freeze input;
receiving, by the at least one processor, a selection of one of the plurality of selectable clinical objects;
retrieving, by the at least one processor, the color flow Doppler profile and the pulsed wave Doppler profile associated with the selected one of the plurality of selectable clinical objects;
acquiring, by the ultrasound system, and presenting, at the display system, color flow Doppler ultrasound data based on the imaging parameters of the retrieved color flow Doppler profile;
initiating, by the at least one processor, a pulsed wave Doppler imaging mode;
acquiring, by the ultrasound system, and presenting, at the display system, pulsed wave Doppler ultrasound data based on the imaging parameters of the retrieved pulsed wave Doppler profile;
receiving, by the at least one processor, the freeze input;
after receiving the freeze input, automatically performing, by the at least one processor, the measurement of the color flow Doppler ultrasound data and/or the pulsed wave Doppler ultrasound data as specified by the one or both of the color flow Doppler profile or the pulsed wave Doppler profile; and
automatically presenting, at the display system, the measurement of the color flow Doppler ultrasound data and/or the pulsed wave Doppler ultrasound data.

2. The method of claim 1, comprising receiving, by the at least one processor, patient information comprising a gestational age of a fetus, wherein the color flow Doppler profile and the pulsed wave Doppler profile are retrieved based in part on the gestational age of the fetus.

3. The method of claim 1, wherein the pulsed wave Doppler imaging mode is initiated in response to receiving a placement of a gate in the color flow Doppler ultrasound data.

4. The method of claim 1, comprising:
initiating, by the at least one processor, a B-mode ultrasound imaging mode prior to presenting the plurality of selectable clinical objects at the display system; and
switching, by the at least one processor, to a color flow Doppler imaging mode after receiving the selection of the one of the plurality of selectable clinical objects.

5. The method of claim 1, wherein the plurality of selectable clinical objects comprises a plurality of:
a uterine artery,
a middle cerebral artery,
an umbilical artery,
a ductus venosis, or
an aorta.

6. The method of claim 1, wherein the imaging parameters of the color flow Doppler profile and the pulsed wave Doppler profile each comprises a plurality of:
a pulse repetition frequency (PRF),
a frequency,
a wall motion filter setting,
a baseline,
a gain, or
a gate size.

7. The method of claim 1, wherein the measurement comprises:
a peak systolic velocity (PS) measurement,
an end-diastolic velocity (ED) measurement,
a min-diastolic velocity (MD) measurement,
a ratio (S/D) of peak systolic velocity to end-diastolic velocity (PS/ED) measurement,
a pulsatility index (PI) measurement,
a resistivity index (RI) measurement, and/or
a time averaged maximum velocity ($TA_{MAX}$) measurement.

8. An ultrasound system comprising:
a display system configured to present a plurality of selectable clinical objects, each of the plurality of selectable clinical objects is a different, specific anatomical structure, each of the plurality of selectable clinical objects associated with a color flow Doppler profile and a pulsed wave Doppler profile, each of the color flow Doppler profile and the pulsed wave Doppler profile comprising imaging parameters for the associated one of the plurality of selectable clinical objects, wherein one or both of the color flow Doppler profile or the pulsed wave Doppler profile specify a measurement of the specific anatomical structure to be automatically performed after receiving a freeze input;
at least one processor configured to:
receive a selection of one of the plurality of selectable clinical objects;
retrieve the color flow Doppler profile and the pulsed wave Doppler profile associated with the selected one of the plurality of selectable clinical objects;
apply the imaging parameters of the retrieved color flow Doppler profile to acquire and present color flow Doppler ultrasound data at the display system;
initiate a pulsed wave Doppler imaging mode;
apply the imaging parameters of the retrieved pulsed wave Doppler profile to acquire and present pulsed wave Doppler ultrasound data at the display system;
receive the freeze input;
automatically perform, after the freeze input is received, the measurement of the color flow Doppler ultrasound data and/or the pulsed wave Doppler ultrasound data as specified by the one or both of the color flow Doppler profile or the pulsed wave Doppler profile; and automatically present, at the display system, the measurement of the color flow Doppler ultrasound data and/or the pulsed wave Doppler ultrasound data.

9. The ultrasound system of claim 8, wherein the at least one processor is configured to receive patient information comprising a gestational age of a fetus, and wherein the color flow Doppler profile and the pulsed wave Doppler profile are retrieved based in part on the gestational age of the fetus.

10. The ultrasound system of claim 8, wherein the at least one processor is configured to initiate the pulsed wave Doppler imaging mode in response to receiving a placement of a gate in the color flow Doppler ultrasound data.

11. The ultrasound system of claim 8, wherein the plurality of selectable clinical objects comprises a plurality of:
a uterine artery,
a middle cerebral artery,
an umbilical artery,
a ductus venosis, or
an aorta.

12. The ultrasound system of claim 8, wherein the imaging parameters of the color flow Doppler profile and the pulsed wave Doppler profile each comprises a plurality of:
a pulse repetition frequency (PRF),
a frequency,
a wall motion filter setting,
a baseline,
a gain, or
a gate size.

13. The ultrasound system of claim 8, wherein the at least one processor is configured to:
initiate a B-mode ultrasound imaging mode prior to presenting the plurality of selectable clinical objects at the display system; and
switch to a color flow Doppler imaging mode after receiving the selection of the one of the plurality of selectable clinical objects.

14. The ultrasound system of claim 8, wherein the measurement comprises:
a peak systolic velocity (PS) measurement,
an end-diastolic velocity (ED) measurement,
a min-diastolic velocity (MD) measurement,
a ratio (S/D) of peak systolic velocity to end-diastolic velocity (PS/ED) measurement,
a pulsatility index (PI) measurement,
a resistivity index (RI) measurement, and/or
a time averaged maximum velocity ($TA_{MAX}$) measurement.

15. A non-transitory computer readable medium having stored thereon, a computer program having at least one code section, the at least one code section being executable by a machine for causing the machine to perform steps comprising:
presenting a plurality of selectable clinical objects at a display system, each of the plurality of selectable clinical objects is a different, specific anatomical structure, each of the plurality of selectable clinical objects associated with a color flow Doppler profile and a pulsed wave Doppler profile, each of the color flow Doppler profile and the pulsed wave Doppler profile comprising imaging parameters for the associated one of the plurality of selectable clinical objects, wherein one or both of the color flow Doppler profile or the pulsed wave Doppler profile specify a measurement of the specific anatomical structure to be automatically performed after receiving a freeze input;
retrieving the color flow Doppler profile and the pulsed wave Doppler profile associated with a selected one of the plurality of selectable clinical objects;
acquiring and presenting, at the display system, color flow Doppler ultrasound data based on the imaging parameters of the retrieved color flow Doppler profile;
initiating a pulsed wave Doppler imaging mode;
acquiring and presenting, at the display system, pulsed wave Doppler ultrasound data based on the imaging parameters of the retrieved pulsed wave Doppler profile;
receiving the freeze input;
after receiving the freeze input, automatically performing the measurement of the color flow Doppler ultrasound data and/or the pulsed wave Doppler ultrasound data as specified by the one or both of the color flow Doppler profile or the pulsed wave Doppler profile; and
automatically presenting, at the display system, the measurement of the color flow Doppler ultrasound data and/or the pulsed wave Doppler ultrasound data.

16. The non-transitory computer readable medium of claim 15, comprising receiving patient information comprising a gestational age of a fetus, wherein the color flow Doppler profile and the pulsed wave Doppler profile are retrieved based in part on the gestational age of the fetus.

17. The non-transitory computer readable medium of claim 15, wherein the pulsed wave Doppler imaging mode is initiated in response to receiving a placement of a gate in the color flow Doppler ultrasound data.

18. The non-transitory computer readable medium of claim 15, comprising:
initiating a B-mode ultrasound imaging mode prior to presenting the plurality of selectable clinical objects at the display system; and
switching to a color flow Doppler imaging mode after receiving a selection of the one of the plurality of selectable clinical objects.

19. The non-transitory computer readable medium of claim 15, wherein the plurality of selectable clinical objects comprises a plurality of:
a uterine artery,
a middle cerebral artery,
an umbilical artery,
a ductus venosis, or
an aorta.

* * * * *